US010669312B2

(12) United States Patent
Chung et al.

(10) Patent No.: US 10,669,312 B2
(45) Date of Patent: Jun. 2, 2020

(54) PEPTIDE FOR SUPPRESSING OSTEOCLAST DIFFERENTIATION AND USE THEREOF

(71) Applicant: CAREGEN CO., LTD., Anyang-si (KR)

(72) Inventors: Yong-Ji Chung, Yongin-si (KR); Eun-Mi Kim, Gunpo-si (KR); Eung-Ji Lee, Anyang-si (KR); Tae-Hoon Lee, Sangju-si (KR); A-Reum Han, Icheon-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 15/875,669

(22) Filed: Jan. 19, 2018

(65) Prior Publication Data
US 2018/0170966 A1 Jun. 21, 2018

Related U.S. Application Data

(62) Division of application No. 14/906,829, filed as application No. PCT/KR2013/009602 on Oct. 25, 2013, now Pat. No. 9,908,916.

(30) Foreign Application Priority Data

Jul. 23, 2013 (KR) .......................... 10-2013-0086939

(51) Int. Cl.
C07K 7/08 (2006.01)
C07K 14/54 (2006.01)
A61K 38/00 (2006.01)

(52) U.S. Cl.
CPC ............ *C07K 7/08* (2013.01); *C07K 14/5403* (2013.01); *A61K 38/00* (2013.01)

(58) Field of Classification Search
None
See application file for complete search history.

(56) References Cited

U.S. PATENT DOCUMENTS

| 5,516,512 | A | * | 5/1996 | Dorssers | C07K 14/5403 424/85.2 |
|---|---|---|---|---|---|
| 5,543,141 | A | | 8/1996 | Braford-Goldberg et al. | |
| 7,115,571 | B1 | | 10/2006 | Wright et al. | |
| 2003/0103936 | A1 | | 6/2003 | Bauer et al. | |
| 2013/0089513 | A1 | | 4/2013 | Chung et al. | |

FOREIGN PATENT DOCUMENTS

| EP | 2606905 A1 | 6/2013 |
|---|---|---|
| EP | 2669294 A1 | 12/2013 |
| KR | 2003-0013189 A | 2/2003 |
| KR | 2008-0093334 A | 10/2008 |
| KR | 2009-0036758 A | 4/2009 |
| KR | 101191733 B1 | 10/2012 |
| WO | WO-2009/094172 A2 | 7/2009 |
| WO | WO-2010/147547 A1 | 12/2010 |

OTHER PUBLICATIONS

Lee et al. (2016, Sci. Rep. 6, 30977; doi: 10.1038/srep30977, pp. 1-13).*
Barhanpurkar et al. (2012, Biochem. Biophys. Res. Commun. 418:669-675).*
Harris et al. (2003, Nature Reviews 2: 214-221).*
Extended European Search Report dated Apr. 6, 2017 for European Patent Application No. 13890027.9, Chung et al., "Peptide for suppressing osteoclast differentiation and use thereof," filed Oct. 25, 2013 (10 pages).
Genbank Accession No. AAC08706.1, dated Mar. 31, 1998, retrieved on Nov. 7, 2016 (1 page).
Genbank Accession No. AAH66274.1, dated Jul. 15, 2016, retrieved on Apr. 21, 2014 (2 pages).
Gupta et al., "IL-3 inhibits human osteoclastogenesis and bone resorption through downregulation of c-Fms and diverts the cells to dendritic cell lineage," J Immunol. 185(4):2261-72 (2010).
International Search Report for International Application No. PCT/KR2013/009602, dated Apr. 22, 2014 (8 pages).
Khapli et al., "IL-3 acts directly on osteoclast precursors and irreversibly inhibits receptor activator of NF-kappa B ligand-induced osteoclast differentiation by diverting the cells to macrophage lineage," J Immunol. 171(1):142-51 (2003).
Office Action dated Nov. 15, 2016 for Japanese Patent Application No. 2016-529692, Chung et al., "Peptide for suppressing osteoclast differentiation and use thereof," filed Oct. 25, 2013 (6 pages).
Ren et al., "Influence of IL-3 functional fragment on cord blood stem cell ex vivo expansion and differentiation," Stem Cell Investig. 3:6 (9 pages) (2016).
Written Opinion for International Application No. PCT/KR2013/009602, dated Apr. 22, 2014 (13 pages).

* cited by examiner

*Primary Examiner* — Elizabeth C. Kemmerer
(74) *Attorney, Agent, or Firm* — Clark & Elbing LLP; Susan M. Michaud

(57) ABSTRACT

The peptide of the present invention performs a function, which is the same as or similar to that of natural interleukin (IL)-3, and has superior skin permeability due to the small size thereof. In addition, the peptide of the present invention suppresses the activation of NF-κB and nuclear transition by inhibiting the receptor activator of nuclear factor kappa-B ligand (RANKL)-RANK signaling pathway, and suppresses the expression of a RANKL or an inflammatory cytokine-induced tartrate-resistant acid phosphatase (TRAP), cathepsin K, or TNF receptor type 1 or type 2, thereby inhibiting osteoclast differentiation depending on the treatment concentration. Moreover, the peptide of the present invention can contribute to osteoblast differentiation by promoting the expression of osteoblast differentiation markers such as osteocalcin (OCN), osteoprotegerin (OPG), bone sialoprotein (BSP), or osteopontin (OPN). Therefore, the superior activity and stability of the peptide of the present invention are useful for medicines, sanitary aids, or cosmetics.

12 Claims, 9 Drawing Sheets

Specification includes a Sequence Listing.

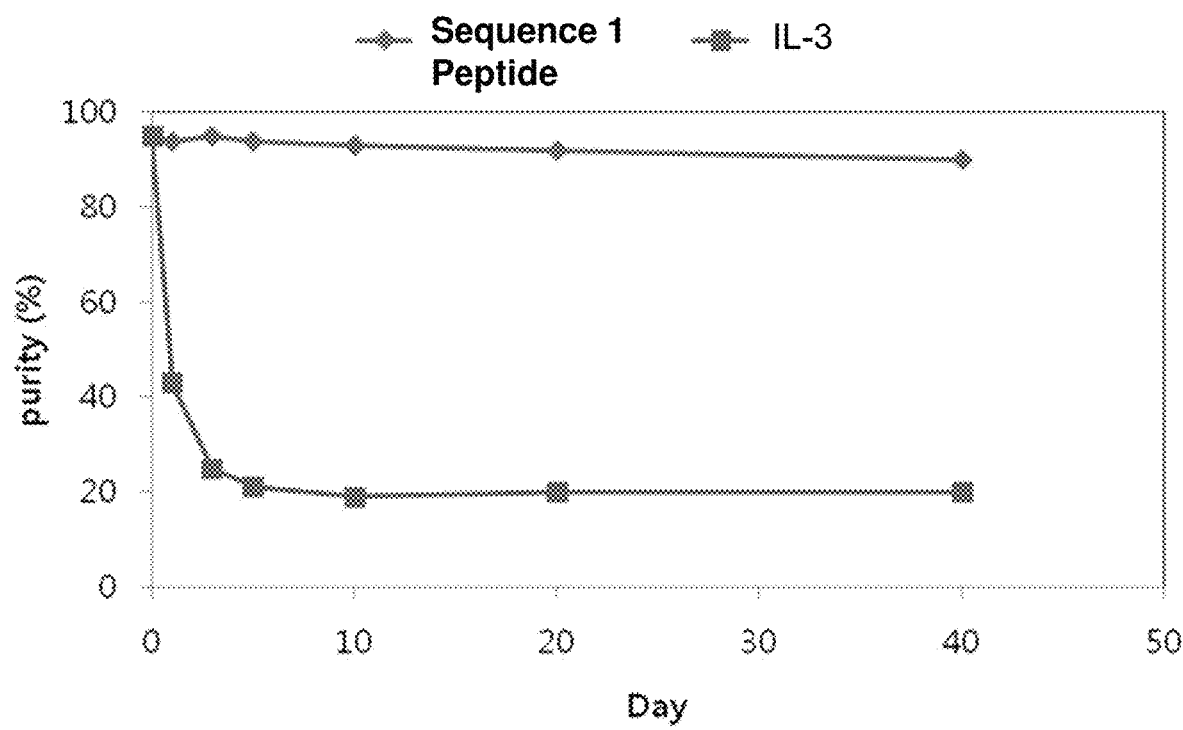
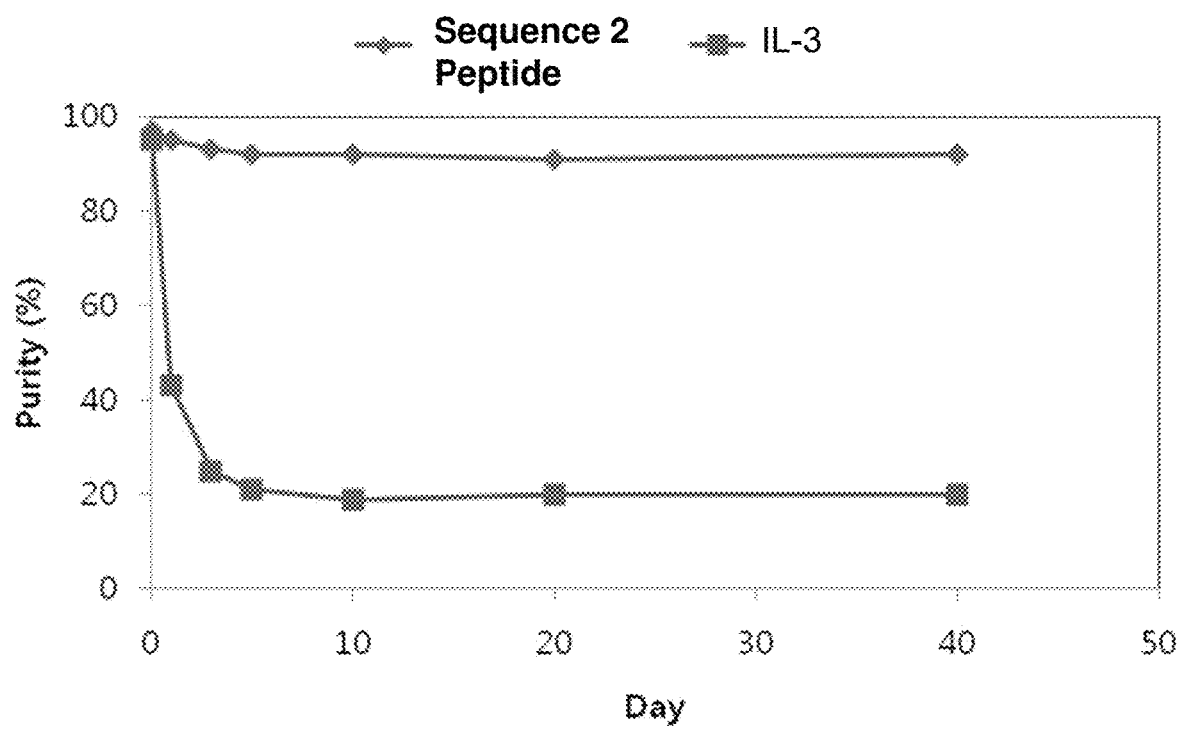

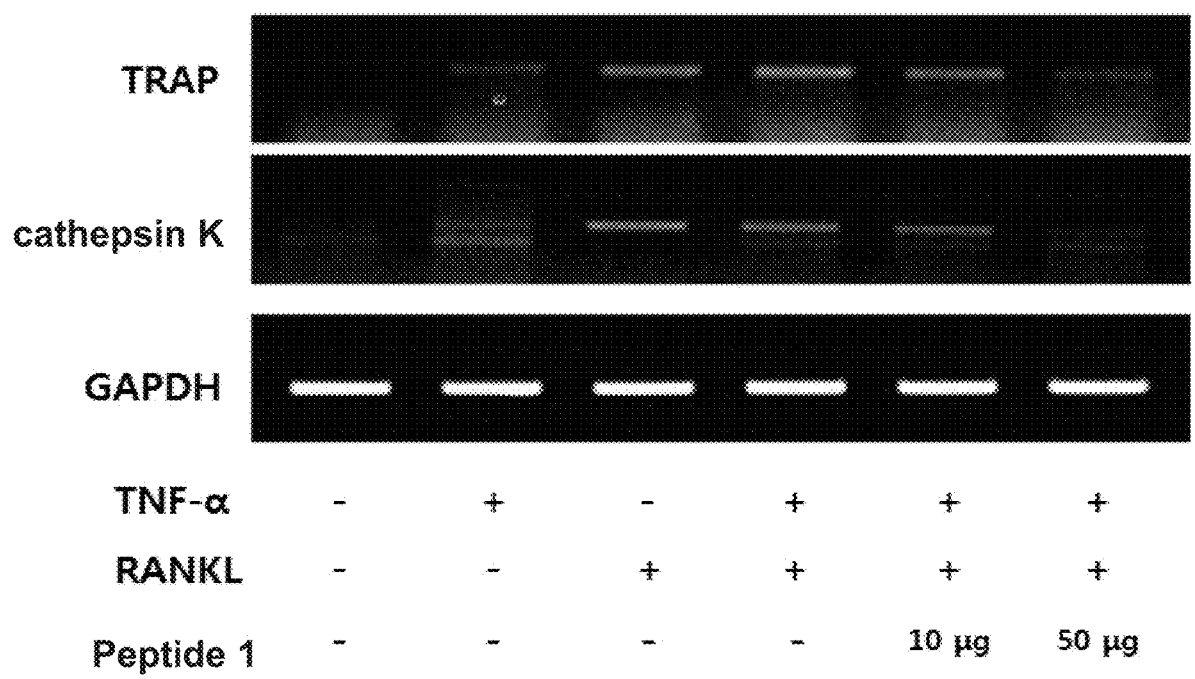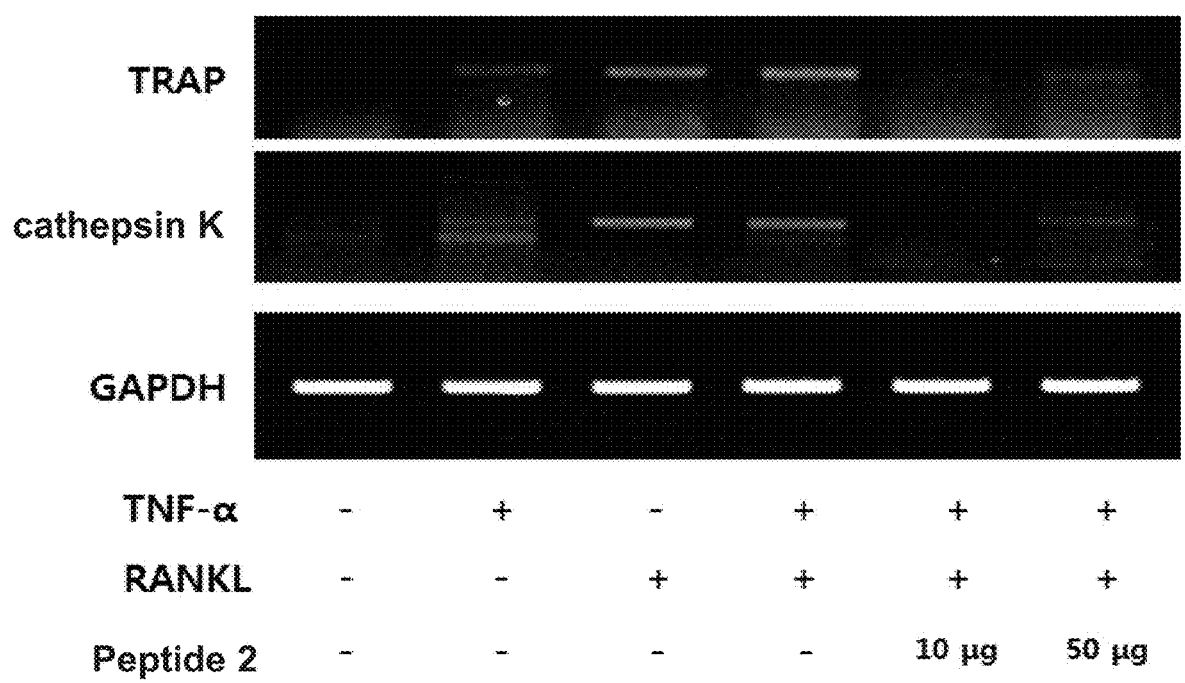

SEQUENCE LISTING

<160> NUMBER OF SEQ ID NOS: 22

<210> SEQ ID NO 1
<211> LENGTH: 12
<212> TYPE: PRT
<213> ORGANISM: Artificial Sequence
<220> FEATURE:

<223> OTHER INFORMATION: IL-3-1 peptide

<400> SEQUENCE: 1

Asn Cys Ser Asn Met Ile Cys Glu Ile Ile Thr His
1               5                   10

<210> SEQ ID NO 2
<211> LENGTH: 12
<212> TYPE: PRT
<213> ORGANISM: Artificial Sequence
<220> FEATURE:
<223> OTHER INFORMATION: IL-3-2 peptide

<400> SEQUENCE: 2

Arg Arg Lys Leu Thr Phe Tyr Leu Lys Thr Leu Glu
1               5                   10

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
aaatcactct ttaagaacag                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
ttattgaata gcagtgacag                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
cctctcttgg tgtccataca                                          20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
atctctctgt accctctgca                                          20

<210> SEQ ID NO 7
<211> LENGTH: 25
<212> TYPE: DNA
<213> ORGANISM: Artificial Sequence
<220> FEATURE:
<223> OTHER INFORMATION: Synthetic Construct

<400> SEQUENCE: 7
ggtgtgaacg gatttggccg tattg                                    25

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8
ccgttgaatt tgccgtgagt ggagt                                    25

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
acctttacgg cttcccagaa                                          20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
tccttacagc cacacaccgt                                          20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
aggctggaaa gcccctaact                                          20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
atgggggtac tggagacagg                                          20

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct

<400> SEQUENCE: 13
cgtgggccgc cctaggca                                            18

<210> SEQ ID NO 14
<211> LENGTH: 20
<212> TYPE: DNA
<213> ORGANISM: Artificial Sequence
<220> FEATURE:

```
<223> OTHER INFORMATION: Synthetic Construct

<400> SEQUENCE: 14
ttggcttagg gttcaggggg                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
gcgctctgtc tctctgacct                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
tttgtaggcg gtcttcaagc                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
ctgcctggga agaagatcag                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
ttgtgaagct gtgcaggaac                                                   20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
aaagtgaagg aaagcgacga                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
gttccttctg cacctgcttc                                                   20
```

```
<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
gatgaatctg acgaatctca c                                          21

<210> SEQ ID NO 22
<211> LENGTH: 21
<212> TYPE: DNA
<213> ORGANISM: Artificial Sequence
<220> FEATURE:
<223> OTHER INFORMATION: Synthetic Construct

<400> SEQUENCE: 22
ctgcttaatc ctcactaaca c                                          21
```

PEPTIDE FOR SUPPRESSING OSTEOCLAST DIFFERENTIATION AND USE THEREOF

SEQUENCE LISTING

The instant application contains a Sequence Listing which has been submitted electronically in ASCII format and is hereby incorporated by reference in its entirety. Said ASCII copy, created on Jul. 29, 2019 is named 51401-003002_Sequence_Listing and is 4,655 bytes in size.

TECHNICAL FIELD

This application claims priority to and the benefit of Korean Patent Application No. 10-2013-0086939 filed in the Korean Intellectual Property Office on 23 Jul. 2013, the entire contents of which are incorporated herein by reference.

The present invention relates to a peptide for inhibiting osteoclast differentiation and a use thereof.

BACKGROUND ART

Bone homeostasis and the skeletal structure are maintained by organized activity between osteoclasts for bone resorption and osteoblasts for bone formation. Osteoclasts, which are multinucleated cells, are differentiated from hematopoietic stem cells [T. Miyamoto, O. Ohneda, F. Arai, et al., Blood 98 (2001) 2544-2554]. The differentiation into osteoclasts is regulated by RANK ligand that is secreted from osteoblasts and activated T lymphocytes [Y. Y. Kong, U. Feige, I. Sarosi, et al., Nature 402 (1999) 304-309].

The receptor activator of nuclear factor kappa-B ligand (RANKL) binds to RANK, which is a receptor that is present in the osteoclast precursor, and osteoclast differentiation is induced in the presence of macrophage-colony stimulating factor (M-CSF). RANKL activates signaling pathways that regulate the formation of osteoclasts and the absorption of bones [J. Li, I. Sarosi, X. Q. Yan, et al., Proc. Natl. Acad. Sci. USA 97 (2000) 1566-1571]. RANK has no tyrosine kinase activity, and induces signaling through adaptor proteins, known as TNF receptor-associated factors (TRAFs) [L. Galibert, M. E. Tometsko, D. M. Anderson, et al., J. Biol. Chem. 273 (1998) 34120-34127]. TRAF6, which is a part of the intercellular molecule, plays a key role in the generation of osteoclasts and activates various downstream signals [M. A. Lomaga, W. C. Yeh, I. Sarosi, et al., Genes Dev. 13 (1999) 1015-1024]. TRAF6 binds to cytoplasmic domains of RANK, and then activates NF-κB and activator protein-1 (AP-1) [S. L. Teitelbaum, J. Clin. Invest. 114 (2004) 463-465].

Tumor necrosis factor-α (TNF-α), which is TNF ligand-based protein, is secreted in several types of cells including monocytes/macrophages or osteoclasts, and induces a number of biological responses through two cell-surface receptors termed TNFR1 and TNFR2 (also called TNFR p55 and TNFR p75, respectively). Both TNFR1 and TNFR2 induce intracellular signals that can stimulate the proteolytic breakdown of kappa B (IκB), a cytoplasmic inhibitor of NF-κB [Verma, I. M., Stevenson, J. K., Schwarz, E. M., Van Antwerp, D., and Miyamoto, S. (1995) Genes Dev. 9, 2723-2735].

TNF-α modulates a varied range of responses, such as inflammation, immune modulation, cell proliferation and differentiation, and apoptosis [Ledgerwood, E. C., Pober, J. S., and Bradley, J. R. (1999) Lab. Invest. 79, 1041-1050]. TNF-α also promotes bone resorption in vitro and in vivo [Bertolini, D. R., Nedwin, G. E., Bringman, T. S., Smith, D. D., and Mundy, G. R. (1986) Nature 319, 516-518], and can induce the secretion of RANKL in osteoblasts [Hofbauer, L. C., Lacey, D. L., Dunstan, C. R., Spelsberg, T. C., Riggs, B. L., and Khosla, S. (1999) Bone 25, 255-259]. In addition, TNF-α is crucial to the pathogenesis of the bone and joint destructions that occur in rheumatoid arthritis, and has been implicated in the bone loss inperiodontitis, orthopedic implant loosening, and other forms of chronic inflammatory osteolysis. TNF-α is mediated by lipopolysaccharide-stimulated osteoclasts [Abu-Amer, Y., Ross, F. P., Edwards, J., and Teitelbaum, S. L. (1997) J. Clin. Invest. 100, 1557-1565]. TNF-α plays an important role in estrogen deficiency-induced bone loss in postmenopausal osteoporosis [Cenci, S., Weitzmann, M. N., Roggia, C., Namba, N., Novack, D., Woodring, J., and Pacifici, R. (2000) J. Clin. Invest. 106, 1229-1237].

Interleukin-3 (IL-3), which is the cytokine secreted mainly by activated T lymphocytes, may be used as a connection link between the immune system and the hematopoietic stem cell system [J. W. Schrader, Interleukin-3, in: A. W. Thomson, M. T. Lotze (Eds.), Academic Press, London, U K, 2003, pp. 201-225]. IL-3 directly acts on mouse osteoclast precursors, and promotes cell differentiation into macrophages, thereby inhibiting the RANKL-induced osteoclast differentiation [S. M. Khapli, L. S. Mangashetti, S. D. Yogesha, M. R. Wani, J. Immunol. 171 (2003) 142-151]. In the osteoclast precursor, IL-3 inhibits the phosphorylation and degradation of IκB, thereby preventing the nuclear translocation of NF-κB, which is induced by RANKL. In addition, IL-3 inhibits RANKL-induced c-Jun N-terminal kinase (JNK) activity, and down-regulates the expression of transcriptional factors, c-Fos and NFATc1. IL-3 inhibits the expression of RANK at the post-transcriptional stage, and this procedure was confirmed to be irreversible, through the in vivo experiment using mice.

Throughout the entire specification, many papers and patent documents are referenced and their citations are represented. The disclosure of the cited papers and patent documents are entirely incorporated by reference into the present specification, and the level of the technical field within which the present invention falls, and the details of the present invention are explained more clearly.

DETAILED DESCRIPTION OF THE INVENTION

Technical Problem

The present inventors have endeavored to develop a material that has excellent activity and stability compared with naturally occurring interleukin-3 (IL-3) protein while retaining the same or similar functions to IL-3. As a result, the present inventors have selected an IL-3-derived peptide having excellent physiological activity (e.g., osteoclast differentiation inhibitory ability, osteogenic differentiation promoting ability, etc.) among a lot of peptide candidates, and have then completed the present invention.

Therefore, an aspect of the present invention is to provide a peptide including an amino acid sequence of SEQ ID NO: 1 or SEQ ID NO: 2.

Another aspect of the present invention is to provide a pharmaceutical composition for alleviating or treating bone diseases.

Still another aspect of the present invention is to provide a composition for promoting osteogenic differentiation.

Still another aspect of the present invention is to provide a method for alleviating or treating bone diseases.

Still another aspect of the present invention is to provide a method for promoting osteogenic differentiation.

Other purposes and advantages of the present disclosure will become more obvious with the following detailed description of the invention, claims, and drawings.

Technical Solution

In accordance with an aspect of the present invention, there is provided a peptide including an amino acid sequence of SEQ ID NO: 1 or SEQ ID NO: 2.

The present inventors have endeavored to develop a material that has excellent activity and stability compared with naturally occurring interleukin-3 (IL-3) protein while retaining the same or similar functions to IL-3. As a result, the present inventors have selected an IL-3-derived peptide having excellent physiological activity (e.g., osteoclast differentiation inhibitory ability, osteogenic differentiation promoting ability, etc.) among a lot of peptide candidates.

The present inventors synthesized a plurality of IL-3-derived peptides that exhibit the above-described characteristics, based on moieties involved in functions of human IL-3. More specifically, the peptide of the present invention was selectively prepared by arbitrarily partial-synthesizing several moieties of IL-3 protein to first search for moieties which is bindable to receptor proteins and then optimizing amino acid sequences of the predicted moieties, and then, of these candidate peptides, the peptides having the most excellent activity were screened, and thus the peptides of SEQ ID NO: 1 and SEQ ID NO: 2 of the present invention were prepared.

According to some embodiments, the peptides of SEQ ID NO: 1 and SEQ ID NO: 2 of the present invention were derived from human IL-3 (GenBank Accession Number, AAH66275.1; SEQ ID NO: 3), which are shown in table 1. The peptides of SEQ ID NO: 1 and SEQ ID NO 2 of the present invention have activity, such as growth factors, by performing similar functions to naturally occurring IL-3 to bind to receptors thereof.

The peptides of the present invention did not only have strong osteoclast differentiation inhibitory ability in a dose-dependent manner, but also significantly promoted osteoblast differentiation (see FIGS. 3 to 8).

According to a certain embodiment of the present invention, the peptides of the present invention inhibit the receptor activator of nuclear factor kappa-B ligand (RANKL)-RANK signaling pathway.

The peptides of the present invention remarkably inhibited RANKL-mediated NF-κB activation and nuclear translocation (see FIGS. 7a and 7b).

According to a certain embodiment of the present invention, the peptides of the present invention inhibit the RANKL- or inflammatory cytokine-induced osteoclast differentiation, and the RANKL- or inflammatory cytokine-induced expressions of tartrate-resistant acid phosphatase (TRAP), cathepsin K, or type 1 or type 2 TNF receptor.

According to a certain embodiment of the present invention, the foregoing inflammatory cytokines include tumor necrosis factor-α (TNF-α), macrophage colony-stimulating factor (M-CSF), interleukin-1β (IL-1β), IL-6, and IL-7; more specifically, TNF-α, IL-1β, and IL-6; still more specifically, TNF-α, and IL-1β; and most specifically, TNF-α.

The peptides of the present invention can promote osteoblast differentiation.

According to a certain embodiment of the present invention, the peptides of the present invention promote the expressions of osteoblast differentiation markers, such as osteocalcin (OCN), osteoprotegerin (OPG), bone sialoprotein (BSP), and osteopontin (OPN).

As used herein, the term "peptide" refers to a molecule in which amino acid residues bind to each other via a peptide linkage. The peptides of the present invention may be prepared by, for example, the solid-phase synthetic method (solid-phase synthesis techniques; Merrifield, *J. Amer. Chem. Soc.* 85:2149-54 (1963); Stewart, et al., *Solid Phase Peptide Synthesis,* 2nd. ed., Pierce Chem. Co.: Rockford, 111 (1984)) or the liquid-phase synthetic method (U.S. Pat. No. 5,516,891).

The peptides of the present invention per se have excellent stability compared with naturally occurring IL-3 protein, but the stability thereof can be further improved through amino acid modification (see FIGS. 2a and 2b).

According to the present invention, the peptides of the present invention have very excellent thermal stability compared with naturally occurring IL-3 protein. The naturally occurring IL-3 protein has low stability in long-term storage and temperature, is difficult to prepare, and has a high production cost. However, the peptides of the present invention can be mass-produced very cheaply, can prevent the deterioration in bioactivity as much as possible due to physiochemical stability thereof at high temperatures, and has further improved therapeutic effects by increasing the remaining period in vivo and in vitro. Therefore, the peptides of the present invention can be favorably applied to products that require long-term storage, such as medicines, quasi-medicines, and cosmetics.

According to a certain embodiment of the present invention, a protective group, which is selected from the group consisting of an acetyl group, a fluorenyl methoxy carbonyl group, a formyl group, a palmitoyl group, a myristyl group, a stearyl group, and polyethylene glycol (PEG), may be linked to the N- or C-terminal of the peptides.

The foregoing amino acid modification significantly improves the stability of the peptides of the present invention. As used herein, the term "stability" refers to storage stability (e.g., room-temperature stability) as well as "in vivo" stability. The foregoing protective group protects the peptides of the present invention from the attack of in vivo protein cleavage enzymes.

In accordance with another aspect of the present invention, there is provided a pharmaceutical composition for alleviating or treating bone diseases, the composition containing the foregoing peptide as an active ingredient.

In accordance with still another aspect of the present invention, there is provided a composition for promoting osteogenic differentiation, the composition containing the peptide as an active ingredient.

Since the composition of the present invention contains the foregoing IL-3-related peptides of the present invention as an active ingredient, descriptions of overlapping contents between the two are omitted to avoid excessive complication of the specification due to repetitive descriptions thereof.

As used herein, the term "bone diseases" refer to diseases, disorders, or conditions associated with RANKL-mediated signaling, and include diseases, disorders, conditions related to the regulation of bone formation and resorption, as well as bone mass reductive disorders, including the reduction of bone mass, osteoporosis, and osteolysis.

According to a certain embodiment of the present invention, the bone diseases, which can be alleviated or treated by the pharmaceutical composition of the present invention, include osteoporosis, childhood osteoporosis, osteogenesis imperfecta, osteomalacia, bone necrosis, rickets, osteomyelitis, alveolar bone loss, Paget's disease, hypercalcemia, primary hyperparathyroidism, metastatic bone diseases, myeloma, bone loss in rheumatoid arthritis, bone loss resulting from cancers, fibrous dysplasia, aplastic bone disease, metabolic bone diseases, or bone loss with age, but are not limited thereto.

The composition of the present invention may be used as a pharmaceutical composition containing: (a) a pharmaceutically effective amount of the foregoing peptide exhibiting IL-3 protein activity, of the present invention; and (b) a pharmaceutically acceptable salt.

As used herein, the term "pharmaceutically effective amount" refers to an amount sufficient to attain efficacy or activity of the foregoing IL-3-related peptide.

The pharmaceutically acceptable carrier contained in the pharmaceutical composition of the present invention is conventionally used for the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain a lubricant, a wetting agent, a sweetening agent, a flavoring agent, an emulsifier, a suspending agent, a preservative, and the like, in addition to the above ingredients. Suitable pharmaceutically acceptable carriers and preparations are described in detail in *Remington's Pharmaceutical Sciences* (19th ed., 1995).

The pharmaceutical composition of the present invention may be administered orally or parenterally, and examples of the parenteral administration may include intravenous, subcutaneous, intramuscular, intraperitoneal, local, and transdermal injections.

The appropriate dose of the pharmaceutical composition of the present invention varies depending on factors, such as the formulating method, manner of administration, patient's age, body weight, gender, morbidity, and food, time of administration, route of administration, excretion rate, and response sensitivity. An ordinarily skilled practitioner can easily determine and prescribe the dose that is effective for the desired treatment or prevention. According to a preferable embodiment of the present invention, the daily dose of the pharmaceutical composition of the present invention is 0.0005-1,000 mg/kg.

In addition, the pharmaceutical composition of the present invention is formulated in a unit dosage form or into a multidose container, using a pharmaceutically acceptable carrier and/or excipient according to the method that is easily conducted by a person having an ordinary skill in the art to which the present invention pertains. Here, the dosage form may be a solution in an oily or aqueous medium, a suspension, an emulsion, an extract, a powder, granules, a tablet, a capsule, or a gel (e.g., a hydrogel), and may further include a dispersant or a stabilizer.

The composition of the present invention may be used as a cosmetic composition containing: (a) a cosmetically effective amount of the foregoing IL-3-derived peptide; and (b) a cosmetically acceptable carrier. As used herein, the term "cosmetically effective amount" refers to an amount that is sufficient to attain the efficacy of the composition of the present invention described above.

The cosmetic composition of the present invention may be formulated into any dosage form that is conventionally prepared, and examples thereof may include a solution, a suspension, an emulsion, a paste, a gel, a cream, a lotion, a powder, a soap, a surfactant-containing cleansing, an oil, a powder foundation, an emulsion foundation, a wax foundation, and a spray, but are not limited thereto. More specifically, the cosmetic composition of the present invention may be prepared in a dosage form of an emollient lotion, nutritional emulsion, nutritional cream, message cream, essence, eye cream, cleansing cream, cleansing foam, cleansing water, facial pack, spray or powder.

In cases where the dosage form of the present invention is a paste, a cream, or a gel, the carrier component thereof may include animal fibers, vegetable fibers, wax, paraffin, starch, tragacanth, cellulose derivatives, polyethylene glycol, silicone, bentonite, silica, talc, or zinc oxide.

In cases where the dosage of the present invention is a powder or a spray, the carrier component thereof may include lactose, talc, silica, aluminum hydroxide, calcium silicate, or a polyamide powder. In cases where the dosage form of the present invention is especially a spray, the dosage form may additionally include a propellant, such as, chlorofluorohydrocarbon, propane/butane, or dimethyl ether.

In cases where the dosage form of the present invention is a solution or an emulsion, the carrier component thereof may include a solvent, a solubilizer, or an emulsifier, for example water, ethanol, isopropanol, ethyl carbonate, ethyl acetate, benzyl alcohol, benzyl benzoate, propylene glycol, 1,3-butyl glycol oil, glycerol fatty esters, polyethylene glycol, or fatty acid esters of sorbitan.

In cases where the dosage form of the present invention is a suspension, the carrier component thereof may include liquid diluents, such as water, ethanol, and propylene glycol; suspending agents, such as, ethoxylated isostearyl alcohol, polyoxyethylene sorbitol ester, and polyoxyethylene sorbitan ester; microcrystalline cellulose; aluminum metal hydroxide; bentonite; agar; or tragacanth.

In cases where the dosage form of the present invention is a surfactant-containing cleansing, the carrier component thereof may include aliphatic alcohol sulfate, aliphatic alcohol ether sulfate, sulfosuccinate monoester, isothinate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, or ethoxylated glycerol fatty acid ester.

The components contained in the cosmetic composition of the present invention include compositions that are commonly used in the cosmetic composition, in addition to the peptides, as active ingredients, and the carrier component thereof, and for example, may include common aids, such as an antioxidant, a stabilizer, a solubilizer, vitamins, a pigment, and a flavor.

In accordance with another aspect of the present invention, there is provided a method for alleviating or treating bone diseases, the method including administering to a subject a composition containing the foregoing peptide as an active ingredient.

In accordance with still another aspect of the present invention, there is provided a method for promoting osteogenic differentiation, the method including contacting cells with a composition containing the foregoing peptide as an active ingredient.

Since the method of the present invention uses the above-described composition, descriptions of overlapping contents between the two are omitted to avoid excessive complication of the specification due to repetitive descriptions thereof.

Advantageous Effects

Features and advantages of the present invention are summarized as follows:

(i) The peptides of the present invention can exert the same or similar functions to naturally occurring interleukin-3 (IL-3), and have very excellent skin penetration due to a small size thereof.

(ii) The peptides of the present invention inhibit the activation and nuclear translocation of NF-κB through the inhibition of the receptor activator of nuclear factor kappa-B ligand (RANKL)-RANK signaling pathway, and inhibit RANKL- or inflammatory cytokine-induced expression of tartrate-resistant acid phosphatase (TRAP), cathepsin K, or type 1 or type 2 TNF receptor, thereby inhibiting osteoclast differentiation, in a concentration-dependent manner.

(iii) Further, the peptides of the present invention can contribute to osteoblast differentiation by promoting the expressions of osteoblast differentiation markers, such as osteocalcin (OCN), osteoprotegerin (OPG), bone sialoprotein (BSP), and osteopontin (OPN).

(iv) Therefore, excellent activity and stability of the peptide of the present invention can be very favorably applied to medicines, quasi-medicines, and cosmetics.

BRIEF DESCRIPTION OF THE DRAWINGS

FIG. 2 illustrates graphs showing stability test results of peptides of SEQ ID NO: 1 (FIG. 2a) and SEQ ID NO: 2 (FIG. 2b) prepared by synthetic example 1 of the present invention.

FIG. 5 illustrates in the inhibitory effects on the mRNA of osteoclast differentiation markers, TRAP and Cathepsin, by a peptide of SEQ ID NO: 1 (FIG. 5a) and a peptide of SEQ ID NO: 2 (FIG. 5b), prepared by synthetic example of the present invention.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

Examples

Synthetic Example 1: Synthesis of Asn-Cys-Ser-Asn-Met-Ile-Cys-Glu-Ile-Ile-Thr-His (SEQ ID NO: 1)

Figure 1A:
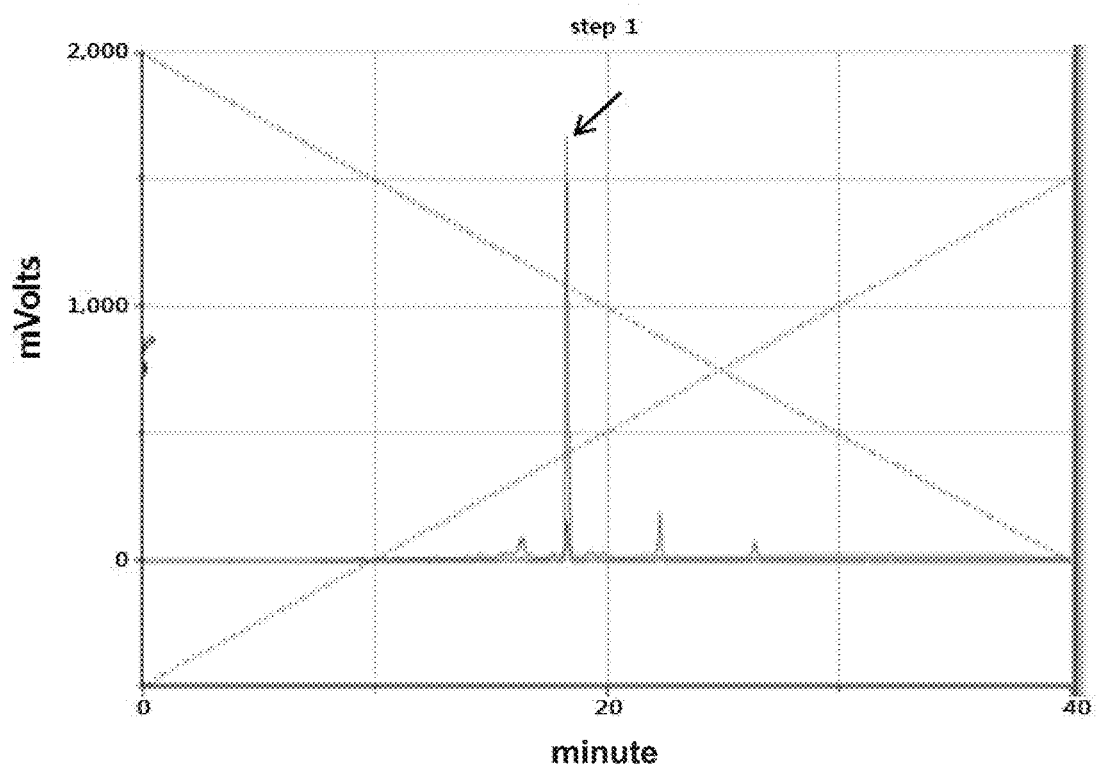
FIG. 1 illustrates graphs showing high-performance liquid-phase chromatography assay results of peptides of SEQ ID NO: 1 (FIG. 1a) and SEQ ID NO: 2 (FIG. 1b) prepared by synthetic example 1 of the present invention.
Figure 1B:
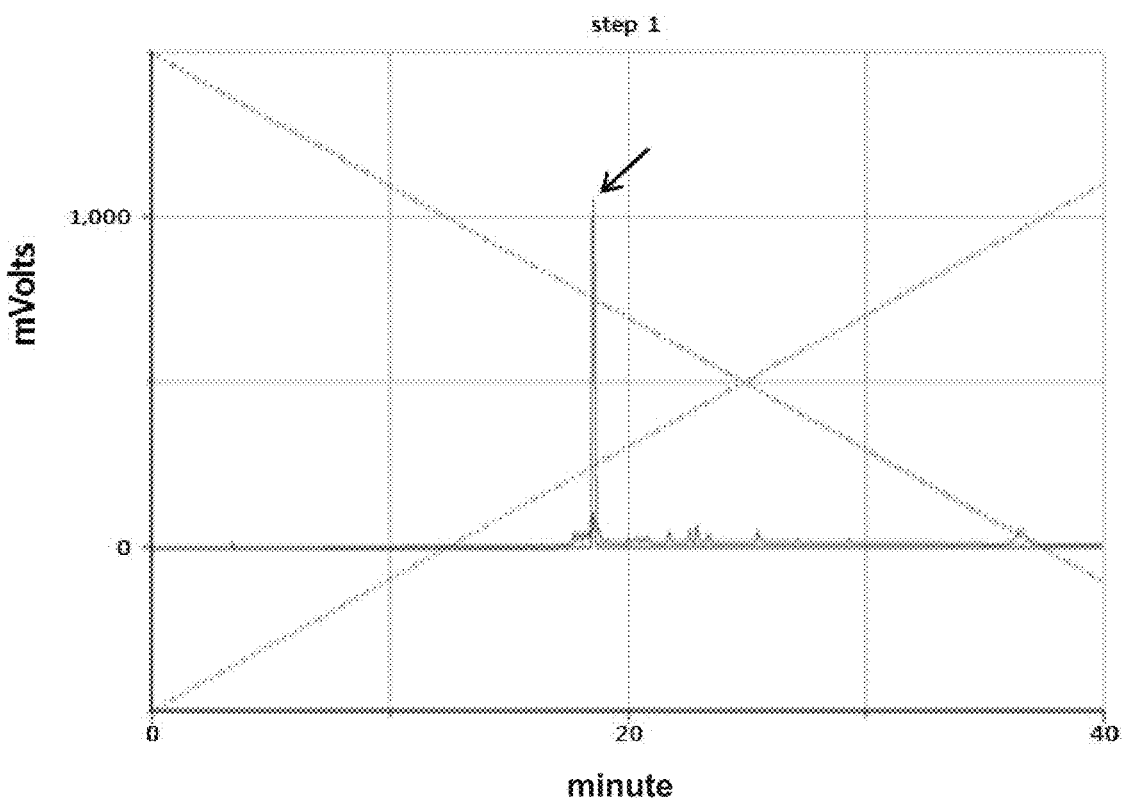

To 700 mg of chloro trityl chloride resin (CTL resin, Nova Biochem Cat No. 01-64-0021) introduced into a reactor was added 10 ml of methylene chloride (MC), followed by stirring for 3 minutes. After removing the solution, 10 ml of dimethylformamide (DMF) was added, followed by stirring for 3 minutes, and then the solvent was again removed. 10 ml of a dichloromethane (DCM) solution was put into the reactor, and 200 mmole Fmoc-L-His(Trt)-OH (Bachem, Swiss) and 400 mmole diisopropyl ethylamine (DIEA) were added, after which the mixture was well dissolved with stirring, and then the reaction was conducted with stirring for 1 hour. After the reaction, the resultant material was washed, and methanol and DIEA (2:1) were dissolved in DCM, followed by a reaction for 10 minutes, and then the resultant material was washed with an excessive amount of DCM/DMF (1:1). After removing the solution, 10 ml of DMF was added, followed by stirring for 3 minutes, and then the solvent was again removed. 10 ml of a deprotection solution (20% piperidine/DMF) was put in the reactor, followed by stirring at room temperature for 10 minutes, and then the solution was removed. The equal amount of a deprotection solution was added, and then the reaction was again maintained for 10 minutes, followed by removal of the solution. The resultant material was washed twice with DMF, once with MC, and once with DMF, for 3 minutes each, thereby preparing His(Trt)-CTL resin. 10 ml of a DMF solution was put in a new reactor, and 200 mmol Fmoc-Thr(tBu)-OH (Bachem, Swiss), 200 mmol HoBt 200 mmole, and 200 mmole Bop were added, and the mixture was dissolved well through stirring. 400 mmole N,N-diisopropylethylamine (DIEA) was divisionally put twice into the reactor, and then the stirring was conducted for at least 5 minutes until all solids were dissolved. The dissolved amino acid mixed solution was put in the reactor containing the deprotected resin, followed by a reaction with stirring at room temperature for 1 hour. After removing the reaction liquid, the stirring was conducted using a DMF solution three times for 5 minutes each, followed by removal. A small amount of the reacted resin was taken to check the reaction degree by Kaiser test (Ninhydrin test). Using the deprotection solution, the deprotection reaction was conducted twice in the same manner as described above, to yield Thr(tBu)-His-(Trt)-CTL resin. After sufficient washing with DMF and MC, Kaiser test was again conducted, and then the following amino acid attachment test was conducted in the same manner as described above. Based on the selected amino acid sequence, the chain reaction was conducted in the order of Fmoc-Ile, Fmoc-Ile, Fmoc-Glu(OtBu), Fmoc-Cys(Trt), Fmoc-Ile, Fmoc-Met, Fmoc-Asn(Trt), Fmoc-Ser(tBu), Fmoc-Cys(Trt), and Fmoc-Asn(Trt). The Fmoc-protective group was removed by reacting twice with the deprotection solution for 10 min each and then conducting washing well. Acetic anhydride, DIEA, and hydroxy benzotriazole (HoBt) were added to conduct acetylation for 1 hour, and then the prepared peptidyl resin was washed three times sequentially with DMF, MC, and methanol, dried under the flow of nitrogen gas, and completely dried by vacuum-drying under phosphorus pentoxide ($P_2O_5$). 30 ml of a leaving solution [95% trifluoroacetic acid (TFA), 2.5% distilled water, and 2.5% thioanisole] was added, and the reaction was maintained for 2 hours while the mixture was intermittently stirred at room temperature. The resin was filtered, washed with a small amount of a solution, and then mixed with stock solution. The distillation was conducted under reduced pressure to reduce the total volume by half, and then 50 ml of cold ether was added to induce precipitation. Thereafter, the precipitates were collected by centrifugation, followed by washing twice with cold ether. After the stock solution was removed, followed by sufficient drying under nitrogen atmosphere, thereby synthesizing 0.5 g of unpurified peptide 1, $NH_2$-Asn-Cys-Ser-Asn-Met-Ile-Cys-Glu-Ile-Ile-Thr-His-OH (SEQ ID NO:1) (yield: 89.9%). The molecular weight was determined as 1375.4 Da (theoretical value: 1377.6 Da) by using a molecular weight analysis system (FIG. 1a). The peptide of SEQ ID NO: 2 ($NH_2$-Arg-Arg-Lys-Leu-Thr-Phe-Tyr-Leu-Lys-Thr-Leu-Glu-OH) was also synthesized by the same method (yield: 92.1%). The molecular weight was determined as 1568.5 Da (theoretical value: 1567.9 Da) by using a molecular weight analysis system (FIG. 1b).

TABLE 1

Sequences and Molecular Weights of Synthesized Peptides

| No. | Amino acid sequence | Analysis value (Mass spectrometer) | |
|---|---|---|---|
| | | Analytic value | Theoretical value |
| IL-3-1 | Asn-Cys-Ser-Asn-Met-Ile-Cys-Glu-Ile-Ile-Thr-His (SEQ ID NO: 1) | 1375.4 | 1377.6 |
| IL-3-2 | Arg-Arg-Lys-Leu-Thr-Phe-Tyr-Leu-Lys-Thr-Leu-Glu (SEQ ID NO: 2) | 1568.5 | 1567.9 |

Test Example 1: Thermal Stability of Prepared Peptides 0.1 mg/ml phosphate buffer solution was prepared from the peptide of SEQ ID NO: 1 or SEQ ID NO: 2, synthesized in synthetic example 1, and standard growth factor (IL-3) purchased from NIBSC (UK). 1 ml of the prepared solution was placed in each glass vial, and allowed to stand at 37° C. The solution standing at 37° C. was sampled on days 0, 1, 3, 5, 10, 20, and 40, and centrifuged for each day to remove denatured peptides or proteins. The supernatant was taken, and quantification using HPLC was conducted (FIGS. 2a and 2b, respectively).

Test Example 2: Verification on Osteoclast Differentiation Inhibitory Effects Using Synthetic Peptides In order to analyze the IL-3-like action and the inhibitory action of the peptides of SEQ ID NO: 1 and SEQ ID NO: 2, synthesized in synthetic example 1, TRAP staining was conducted using Raw264.7 strain differentiable into osteoclasts while referring to methods, such as tartrate-resistant acid phosphatase staining (Rizzino, et al. *Cancer Res.* 48:4266(1988)).

Raw264.7 cell lines (ATCC) were cultured in Dulbecco's modified Eagle's medium (DMEM, Gibco, U.S.A.) supplemented with 10% fetal bovine serum (FBS, Sigma) using each 250 ml-flask for tissue culture. The cultured cell lines were carefully detached from the bottom of the culture container using a pipette, followed by centrifugation, to obtain only cell precipitates. The cell precipitates were re-suspended in DMEM culture medium supplemented with 10% FBS, and then added to a 46-well plate for tissue culture plate at $1 \times 10^4$ cells per each well. For the induction of differentiation, the blank sample and RAW264.7 cells were treated with 10 ng/ml RANKL, 50 ng/ml TNF-α, and 1 μg/ml or 10 μg/ml synthesized peptides dissolved in 10% distilled water in a sterile state, and then cultured under 5% $CO_2$ at 37° C. for 72 hours. After 72 hours, the medium was changed with the same culture liquid, and then the blank sample and the cells were treated with 10 ng/ml RANKL, 50 ng/ml TNF-α, and 1 μg/ml or 10 μg/ml synthesized peptides, and then cultured under the same conditions for 48 hours. After the culturing was completed for a total of five days, the upper layer was removed. For cell fixation, a fixation buffer containing 25 ml of a citrate solution, 65 ml of acetone, and 8 ml of 37% formaldehyde was prepared. The cells were fixed with the fixation buffer for 30 seconds, and then washed three times with phosphate buffer saline (PBS). The washing solution was removed, and the cells were stained with the leukocyte alkaline phosphatase kit (Sigma, U.S.A.).

Figure 3A:
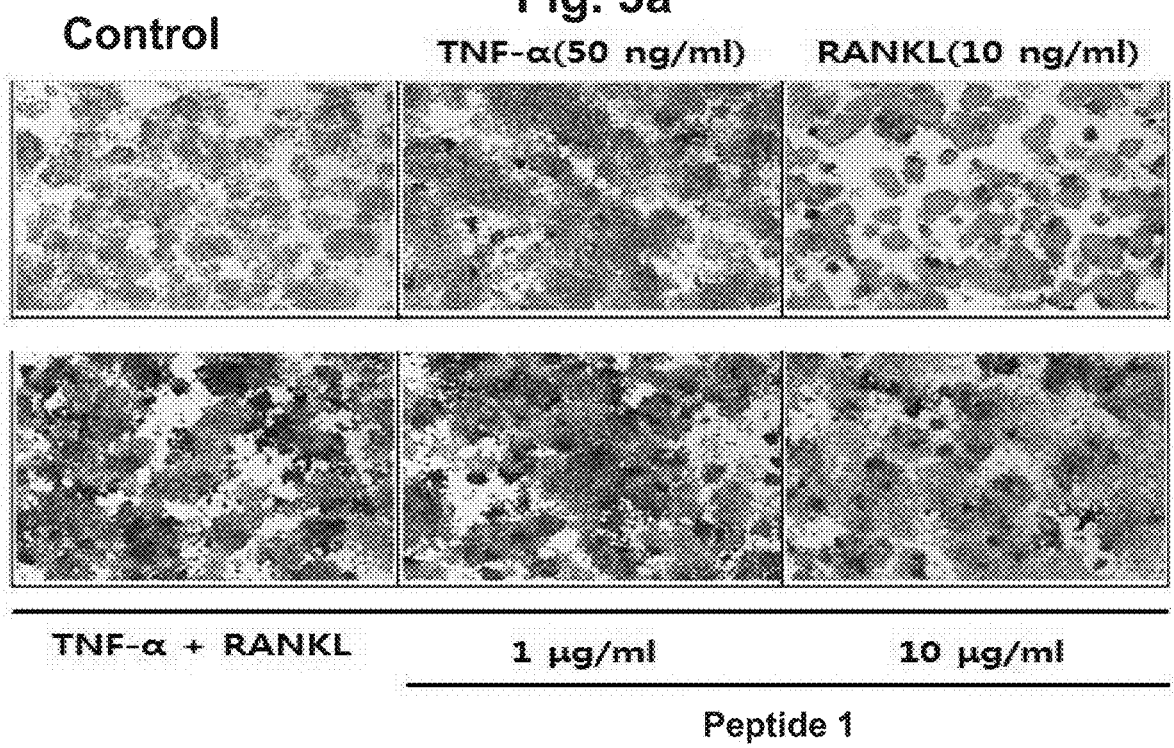
FIG. 3 illustrates osteoclast differentiation inhibitory effects by the treatment with a peptide of SEQ ID NO: 1 (FIG. 3a) and a peptide of SEQ ID NO: 2 (FIG. 3b), prepared by synthetic example of the present invention.
Figure 3B:
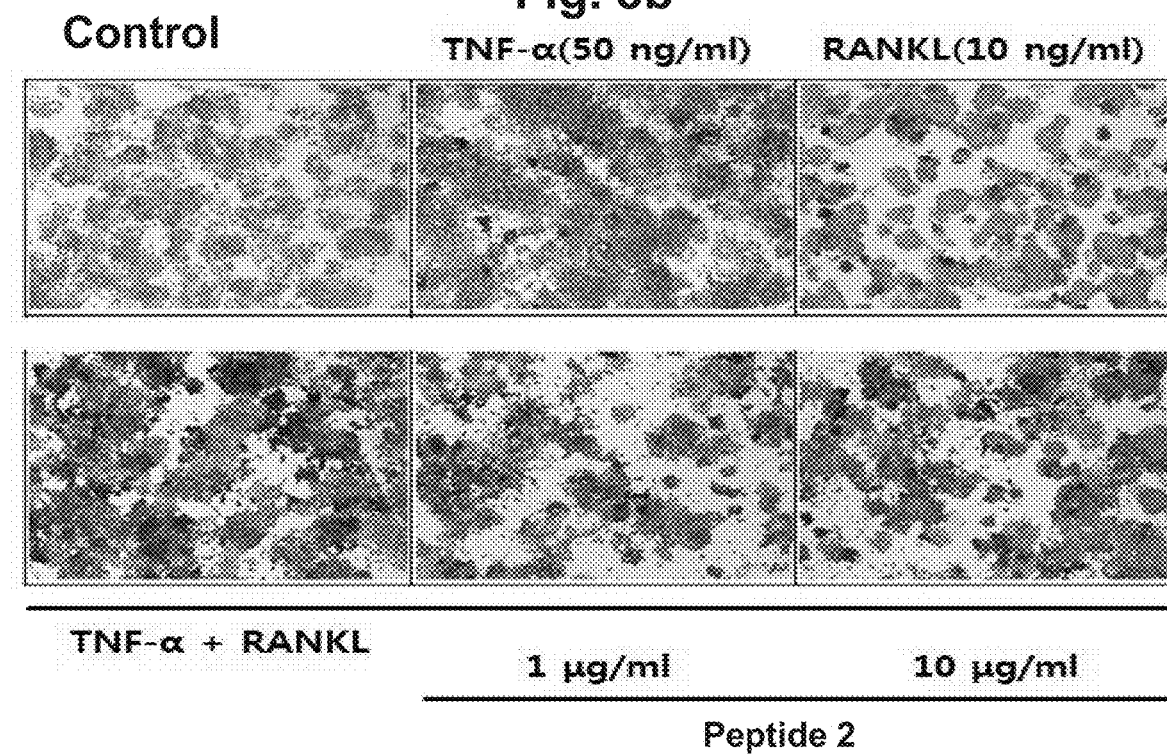

FIG. 3 illustrates the inhibitory results of the differentiation of Raw264.7 cells, of which the differentiation can be induced by RANKL and TNF-α, by IL-3-1 (FIG. 3a) and IL-3-2 (FIG. 3b). As shown in FIGS. 3a and 3b, the peptides of the present invention can inhibit the RANKL- and TNF-α-induced differentiation of Raw264.7 into osteoclasts.

Figure 4A:
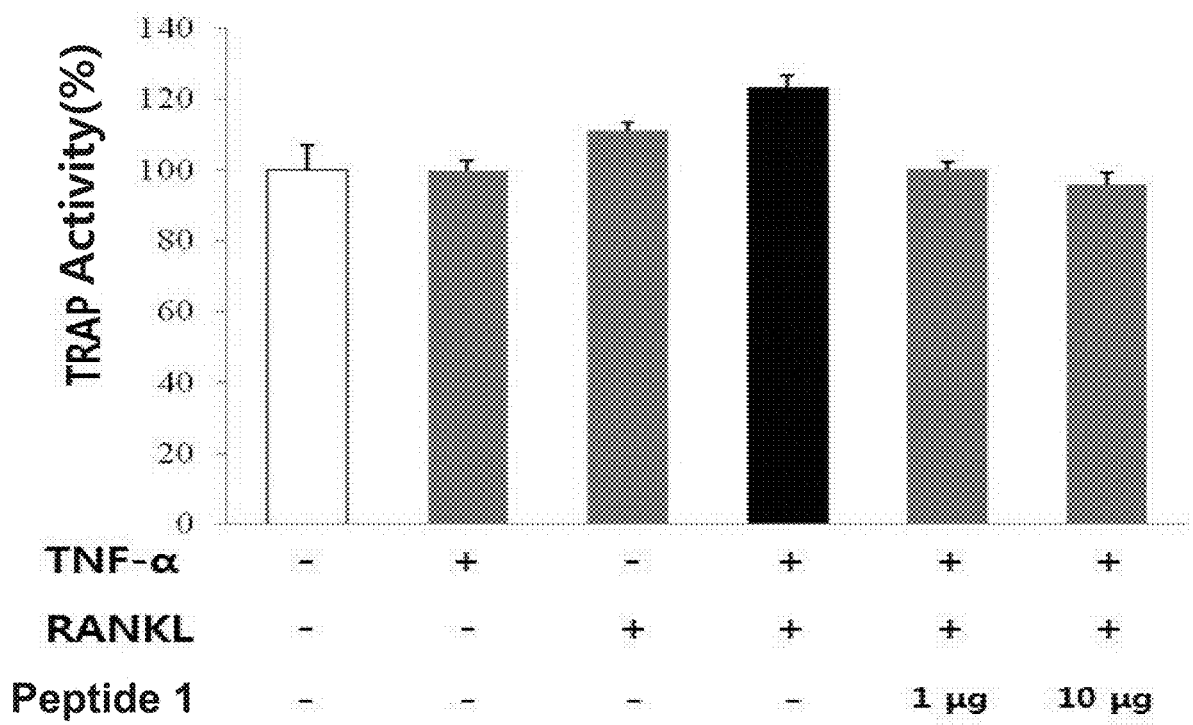
FIG. 4 illustrates the inhibitory effect on the osteoclast differentiation promoting enzyme by the treatment with a peptide of SEQ ID NO: 1 (FIG. 4a) and a peptide of SEQ ID NO: 2 (FIG. 4b), prepared by synthetic example of the present invention.
Figure 4B:
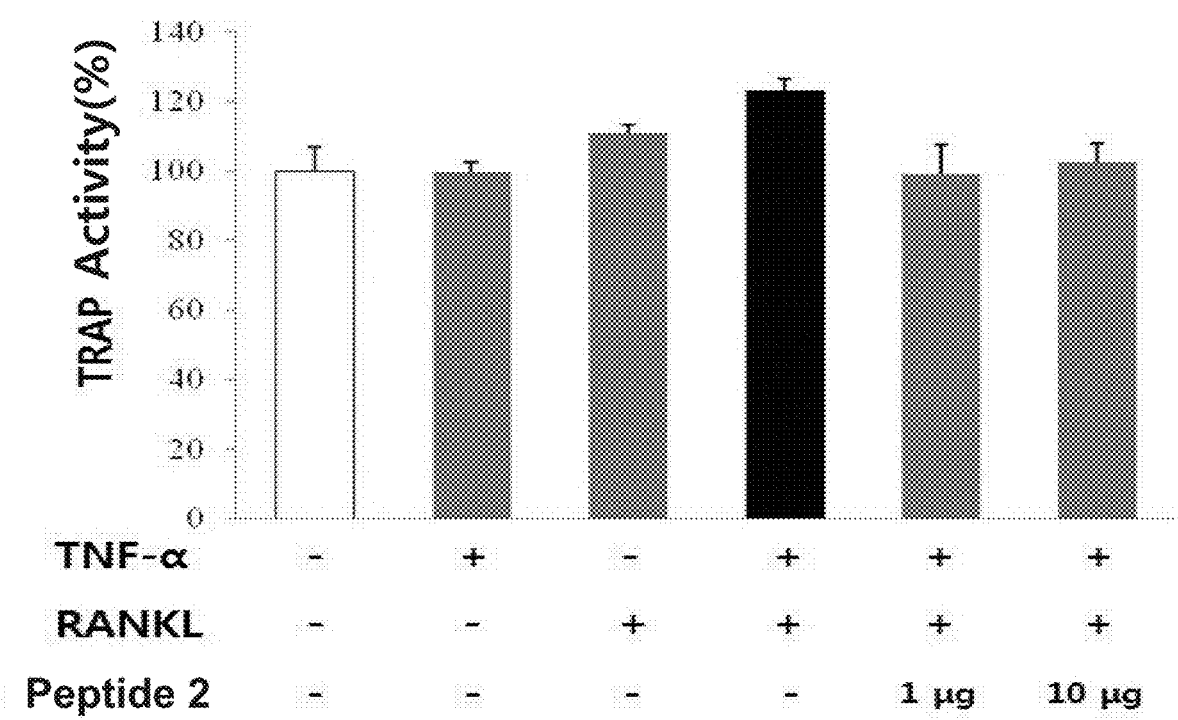

Test Example 3: Verification on Osteoclast Differentiation Inhibitory Effects Using Synthetic Peptides Raw264.7 cells were treated in combination with 10 ng/ml RANKL, 50 ng/ml TNF-α, or the 1 or 10 μg/ml peptide synthesized in synthetic example 1 to induce differentiation for five days, and then the inhibition degree of the activity of TRAP, an osteoclast differentiation marker, was tested. After culture, the culture liquid was removed, and then 100 μl of a lysis buffer (20 mM tris buffer, 3% triton X-100) was added to disrupt cell walls. A reaction solution is prepared from 500 μl of a citrate solution (18 mM citric acid, 9 mM sodium chloride, 12 mM surfactant; pH 3.5), 50 μl of a tartrate solution, and 500 μl of a 20 mM phosphate substrate. 100 μl of the lysate and 100 μl of the reaction solution were added in the same amount, and then the reaction was conducted at 37° C. for 30 minutes. For colorimetric analysis, the absorbance was determined at 405 nm using a spectrophotometer. It was validated that, in cases where the treatment with the peptide of SEQ ID NO: 1 or SEQ ID NO: 2 together with RANKL and TNF-α, the peptides inhibited the activity of TRAP, which is an osteoclast differentiation marker, in a concentration-dependent manner (FIGS. 4a and 4b).

Figure 6A:
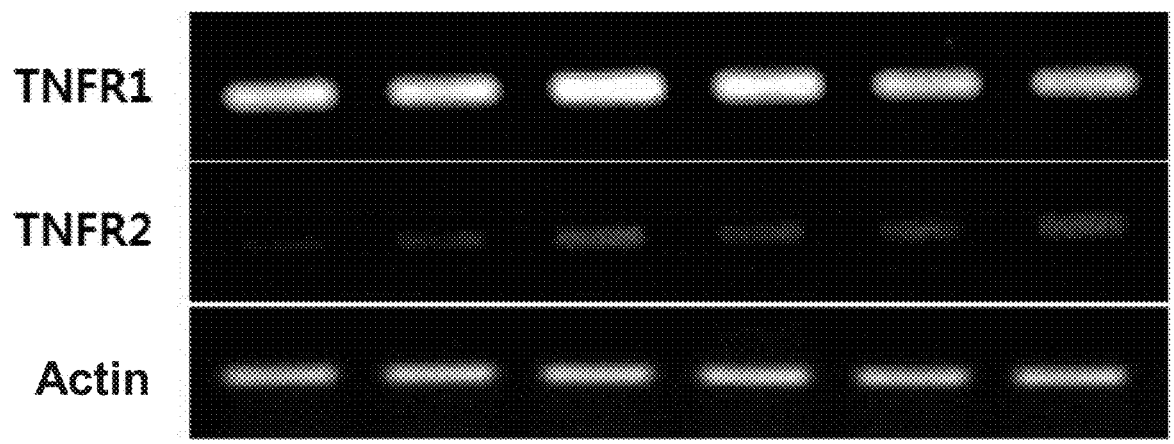
FIG. 6 illustrates the inhibitory effects on the mRNA of type 1 and type 2 TNF receptors by the treatment with a peptide of SEQ ID NO: 1 (FIG. 6a) and a peptide of SEQ ID NO: 2 (FIG. 6b), prepared by synthetic example of the present invention.
Figure 6B:
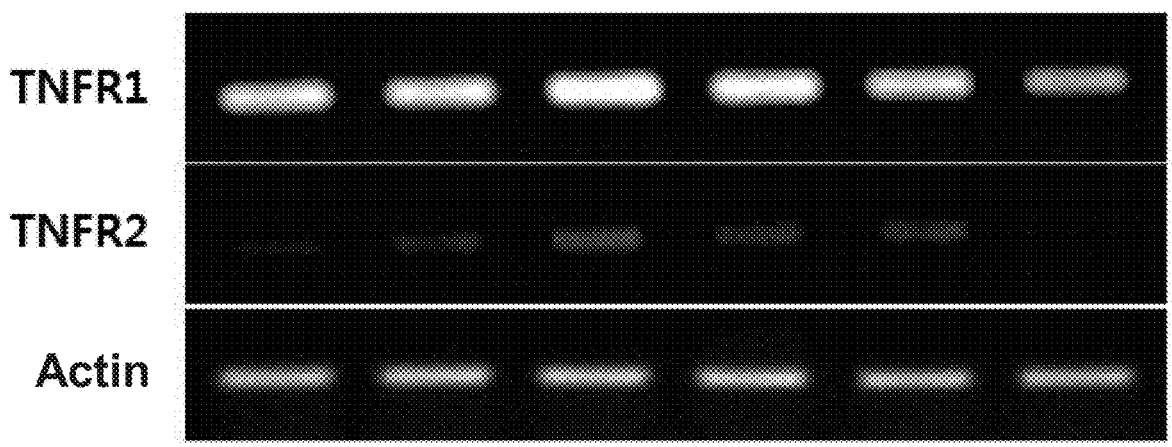

Test Example 4: Verification on Inhibitory Effect on Osteoclast Differentiation Marker mRAN Using Synthetic Peptides Raw264.7 cells were treated in combination with 10 ng/ml RANKL, 50 ng/ml TNF-α, or the 1 or 10 µg/ml peptide synthesized in synthetic example 1 to induce differentiation for five days, and then the inhibition degree of the cathepsin K mRNA expression was analyzed. FIGS. 5a and 5b show that the mRNA levels of cathepsin K were reduced by the treatment with the peptides of the present invention, respectively. In addition, FIGS. 6a and 6b verifies that the mRNA expression levels of type 1 and type 2 TNF receptors, which have been increased by the treatment with RANKL or TNF-α, were reduced by the treatment with all the peptides of the present invention.

Target-specific primer sequences used in PCR were as follows: TRAP forward primer sequence, 5'-AAATCACTCTTTAAGAACAG-3' (SEQ ID NO:3) and TRAP reverse primer sequence, 5'-TTATTGAATAGCAGTGACAG-3' (SEQ ID NO:4) (annealing temperature, 45° C.); cathepsin K forward primer sequence, 5'-CCTCTCTTGGTGTCCATACA-3' (SEQ ID NO:5) and cathepsin K reverse primer sequence, 5'-ATCTCTCTGTACCCTCTGCA-3' (SEQ ID NO:6) (annealing temperature, 53° C.); GAPDH forward primer sequence, 5'-GGTGTGAACGGATTTGGCCGTATTG-3' (SEQ ID NO:7) and GAPDH reverse primer sequence, 5'-CCGTTGAATTTGCCGTGAGTGGAGT-3' (SEQ ID NO:8) (annealing temperature, 55° C.); type 1 TNF receptor forward primer sequence, 5'-acctttacggcttcccagaa-3' (SEQ ID NO:9) and type 1 TNF receptor reverse primer sequence, 5'-tccttacagccacacaccgt-3' (SEQ ID NO:10) (annealing temperature, 55° C.); type 2 TNF receptor forward primer sequence, 5'-aggctggaaagcccctaact-3' (SEQ ID NO:11) and type 2 TNF receptor reverse primer sequence, 5'-atgggggtactggagacagg-3' (SEQ ID NO:12) (annealing temperature, 55° C.); and actin forward primer sequence, 5'-CGTGGGCCGCCCTAGGCA-3' (SEQ ID NO:13) and actin reverse primer sequence, 5'-TTGGCTTAGGGTTCAGGGGG-3' (SEQ ID NO:14) (annealing temperature, 55° C.).

Therefore, the peptides of the present invention can inhibit all of TRAP, cathepsin K, and type 1 and type 2 TNF receptors, which are increased by RANKL and TNF-α (FIGS. 5a and 5b and FIGS. 6a and 6b).

Figure 7A:
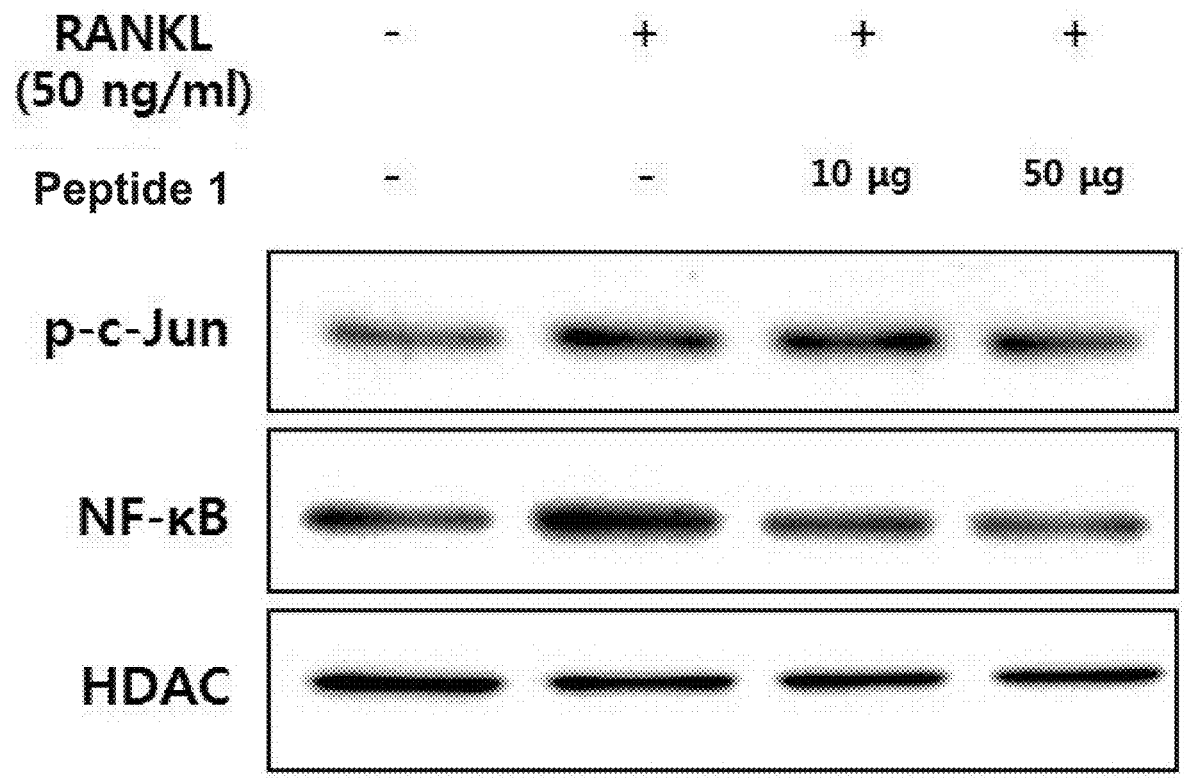
FIG. 7 illustrates RANKL signal inhibitory effects by the treatment with a peptide of SEQ ID NO: 1 (FIG. 7a) and a peptide of SEQ ID NO: 2 (FIG. 7b), prepared by synthetic example of the present invention.
Figure 7B:
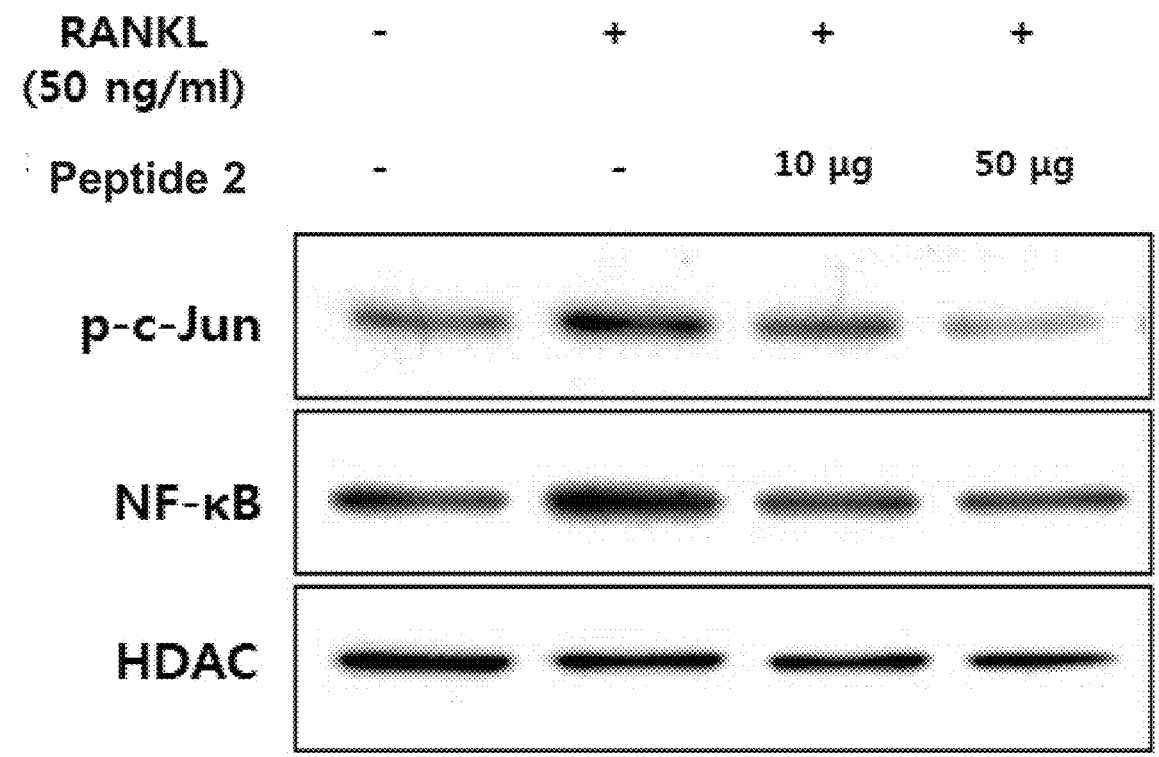

Test Example 5: Verification on RANKL Signal Inhibition by Synthetic Peptides Raw264.7 cells were treated with the peptides synthesized in synthetic example 1, and after 30 minutes, the nuclear translocation of NF-κB, which is a representative signal of RANKL protein, was checked. The effect of each peptide was verified through western blotting using polyclonal antibody to NF-κB (Cat. No sc-372, SantaCruz, USA). The treatment with the peptides of the present invention confirmed the activation and nuclear translocation of NF-κB (FIGS. 7a and 7b). The phosphorylation of c-Jun, which is another representative signal of RANKL protein, and the nuclear translocation of the phosphorylated c-Jun were confirmed. The effect of each peptide was verified through western blotting using polyclonal antibodies to phospho-c-Jun (Cat. No sc-1694, SantaCruz, USA) (FIGS. 7a and 7b).

Considering the test results of test examples 1 to 5, the peptides of the present invention inhibit osteoclast differentiation very effectively through the inhibition of RANKL-RANK signaling activation.

Figure 8A:
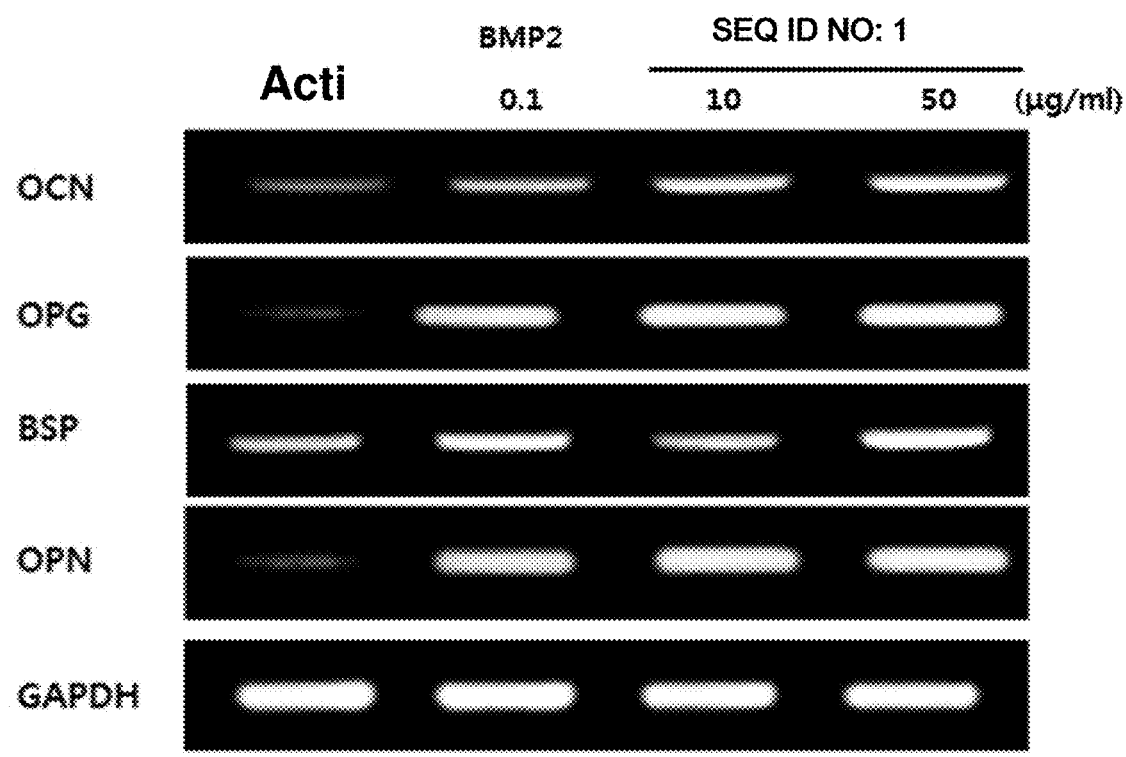
FIG. 8 illustrates osteoblast differentiation promotion results by the treatment with a peptide of SEQ ID NO: 1 (FIG. 8a) and a peptide of SEQ ID NO: 2 (FIG. 8b), prepared by synthetic example of the present invention.
Figure 8B:
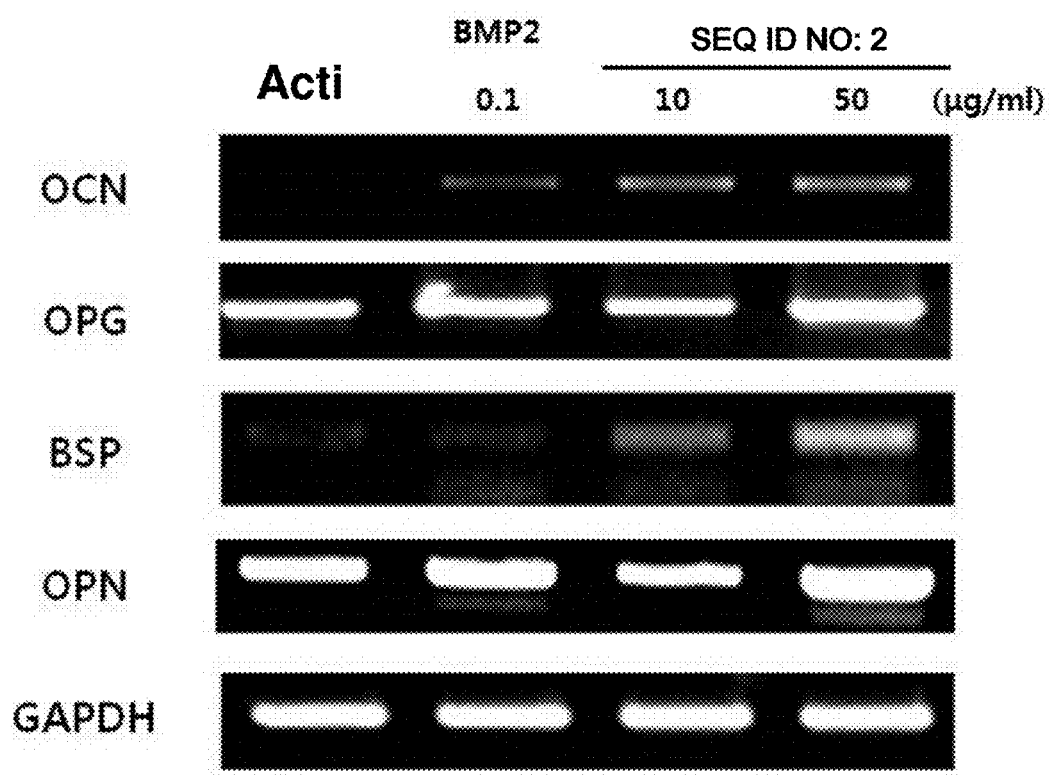

Test Example 6: Verification on Promotion of Osteogenic Differentiation Marker Gene by Synthetic Peptides MC3T3-E1 cells were treated with 10 or 50 µg/ml of the peptides synthesized in synthetic example 1 to induce the differentiation for two days, and tests for verifying the mRNA expression of osteoblast differentiation markers, such as osteocalcin (OCN), osteoprotegerin (OPG), bone sialoprotein (BSP), and osteopontin (OPN), were conducted. Target-specific primer sequences used in PCR were as follows: OCN forward primer sequence, 5'-gcgctctgtctctct-gacct-3' (SEQ ID NO:15) and OCN reverse primer sequence, 5'-tttgtaggcggtcttcaagc-3' (SEQ ID NO:16) (annealing temperature, 60° C.); OPG forward primer sequence, 5'-ctgcctgggaagaagatcag-3' (SEQ ID NO:17) and OPG reverse primer sequence, 5'-ttgtgaagctgtgcaggaac-3' (SEQ ID NO:18) (annealing temperature, 60° C.); BSP forward primer sequence, 5'-aaagtgaaggaaagcgacga-3' (SEQ ID NO:19) and BSP reverse primer sequence, 5'-gttccttctg-cacctgcttc-3' (SEQ ID NO:20) (annealing temperature, 60° C.); OPN forward primer sequence, 5'-GATGAATCTGACGAATCTCAC-3' (SEQ ID NO:21) and OPN reverse primer sequence, 5'-CTGCTTAATCCTCACTAACAC-3' (SEQ ID NO:22) (annealing temperature, 50° C.). FIG. 8 shows that, when the cells were treated with the peptides of the present invention, the mRNA levels of the genes, which are the osteoblast differentiation markers, were increased by the peptides of SEQ ID NO: 1 or SEQ ID NO: 2. Therefore, the peptides of the present invention can promote osteoblast differentiation by increasing the genetic expressions of OCN, OPG, BSP, and OPN, which are osteoblast differentiation markers.

Test Example 7: Verification on Promotion of Osteogenic Differentiation Signal by Synthetic Peptides In order to verify whether pSmad1/5/8, which is a signal involved in osteogenic differentiation, was activated by the present peptides, MC3T3-E1 cells were dispensed into 6-well plates at $2\times10^5$ cells, and then cultured for 24 hours under the conditions of 37° C. and 5% $CO_2$. After 24 hours, the medium was changed with a serum-free medium, and then the cells were starved for 24 hours, treated with the 10 µg/ml peptides or 50 ng/ml BMP2, used as a positive control, for 30 minutes, washed with PBS, and dissolved in a lysis buffer, thereby obtaining proteins, which were then subjected to western blotting.

Figure 9A:
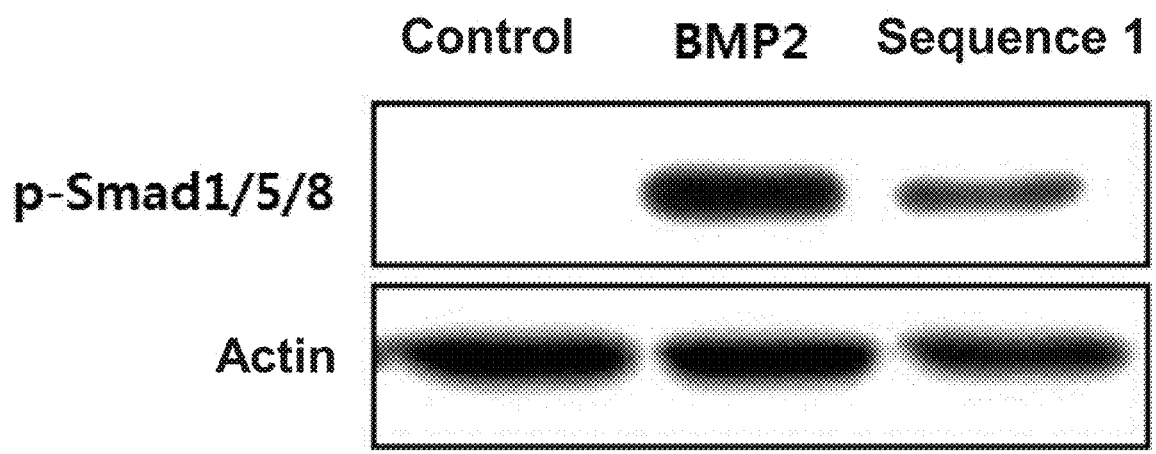
FIG. 9 illustrates that the treatment with a peptide of SEQ ID NO: 1 (FIG. 9a) and a peptide of SEQ ID NO: 2 (FIG. 9b), prepared by synthetic example of the present invention, increased the expression of p-Smad1/5/8, which is a BMP2 signal.
Figure 9B:
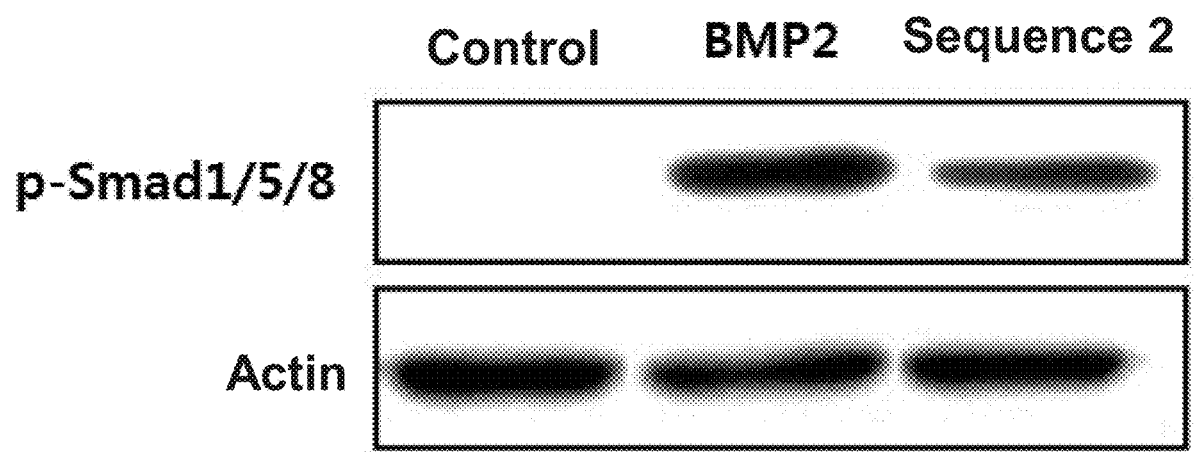

In accordance with the foregoing results, it was confirmed that the treatment with the peptides of SEQ ID NO: 1 or SEQ ID NO: 2 of the present invention led to the phosphorylation of Smad1/5/8, and this means that the bone formation promoting signal is transmitted due to the treatment with the peptides of the present invention, so that the osteoblast differentiation is maintained (FIGS. 9a and 9b, respectively).

Formulation Example 1: Emollient Lotion

Emollient lotion, which includes nanosomes containing peptide 1 or 2, prepared in synthetic example 1, and has the following composition, was prepared by a general skin lotion preparation method.

TABLE 2

Emollient Lotion Composition

| Component | Content (wt %) |
|---|---|
| peptide nanosome | 0.001 |
| 1,3-butylene glycol | 6.0 |
| glycerin | 4.0 |
| PEG 1500 | 1.0 |
| sodium hyaluronate | 1.0 |
| polysolvate 20 | 0.5 |
| ethanol | 8.0 |
| preservative, coloring | Suitable |
| benzophenone-9 | 0.05 |
| aroma | Small |
| purified water | balanced |
| Total | 100 |

Formulation Example 2: Moisturizing Cream

Nutritional cream, which includes nanosomes containing peptide 1 or 2, prepared in synthetic example 1, and has the following composition, was prepared by a general moisturizing cream preparation method.

TABLE 3

Moisturizing Cream Composition

| Component | Content (wt %) |
|---|---|
| peptide nanosome | 0.001 |
| meadowfoam oil | 3.0 |
| cetearyl alcohol | 1.5 |
| stearic acid | 1.5 |
| glyceryl stearate | 1.5 |
| Liquid paraffin | 10.0 |
| wax | 2.0 |
| Polysolvate 60 | 0.6 |
| sorbitan sesquioleate | 2.5 |
| squalane | 3.0 |
| 1,3-butylene glycol | 3.0 |
| glycerin | 5.0 |
| triethanolamine | 0.5 |
| tocopheryl acetate | 0.5 |
| preservative, coloring | suitable |
| aroma | suitable |
| purified water | blanced |
| Total | 100 |

Formulation Example 3: Moisturizing Skin Lotion

Nutritional skin lotion, which includes nanosomes containing peptide 1 or 2, prepared in synthetic example 1, and has the following composition, was prepared by a general skin lotion preparation method.

TABLE 4

Moisturizing Skin Lotion Composition

| Component | Content (wt %) |
|---|---|
| peptide nanosome | 0.002 |
| 1,3-butylene glycol | 4.0 |
| glycerin | 4.0 |
| stearyl alcohol | 0.8 |
| glyceryl stearate | 1.0 |
| Triethanolamine | 0.13 |
| tocopheryl acetate | 0.3 |
| liquid paraffin | 5.0 |
| squalane | 3.0 |
| macadamia nut oil | 2.0 |
| Polysolvate 60 | 1.5 |
| sorbitan sesquioleate | 0.5 |
| carboxy vinly polymer | 1.0 |
| preservative, coloring | suitable |
| aroma | suitable |
| purified water | blanced |
| Total | 100 |

Formulation Example 4: Essence

Essence, which includes nanosomes containing peptide 1 or 2, prepared in synthetic example 1, and has the following composition, was prepared by a general essence preparation method.

TABLE 5

Essence Composition

| Component | Content (wt %) |
|---|---|
| peptide nanosome | 0.005 |
| glycerin | 10.0 |
| 1,3-butylene glycol | 5.0 |
| PEG 1500 | 2.0 |
| allantoin | 0.1 |
| DL-panthenol | 0.3 |
| EDTA-2Na | 0.02 |
| hydroxyethyl cellulose | 0.1 |
| sodium hyaluronate | 8.0 |
| carboxy vinyl polymer | 0.2 |
| triethanolamine | 0.18 |
| octyldodeces-16 | 0.4 |
| ethanol | 6.0 |
| aroma, preservative, coloring | suitable |
| purified water | balanced |
| Total | 100 |

Although the present invention has been described in detail with reference to the specific features, it will be apparent to those skilled in the art that this description is only for one embodiment and does not limit the scope of the present invention. Thus, the substantial scope of the present invention will be defined by the appended claims and equivalents thereof.

The invention claimed is:

1. A peptide consisting of the amino acid sequence of SEQ ID NO: 2.

2. The peptide of claim 1, wherein the peptide inhibits the receptor activator of nuclear factor kappa-B ligand (RANKL)-RANK signaling pathway.

3. The peptide of claim 1, wherein the peptide inhibits RANKL- or inflammatory cytokine-induced osteoclast differentiation.

4. The peptide of claim 1, wherein the peptide inhibits the RANKL- or inflammatory cytokine-induced expression of tartrate-resistant acid phosphatase (TRAP), cathepsin K, or type 1 or type 2 TNF receptor.

5. The peptide of claim 3, wherein the inflammatory cytokine includes tumor necrosis factor-α (TNF-α), macrophage colony-stimulating factor (M-CSF), interleukin-1β (IL-1β), IL-6 or IL-7.

6. The peptide of claim 1, wherein the peptide promotes osteoblast differentiation.

7. The peptide of claim 1, wherein the N- or C-terminal of the peptide is linked to a protective group selected from the group consisting of an acetyl group, a fluorenyl methoxy carbonyl group, a formyl group, a palmitoyl group, a myristyl group, a stearyl group and polyethylene glycol (PEG).

8. A peptide consisting of the amino acid sequence of SEQ ID NO: 2, wherein a protective group selected from the group consisting of an acetyl group, a fluorenyl methoxy carbonyl group, a formyl group, a palmitoyl group, a myristyl group, a stearyl group, and polyethylene glycol (PEG), is linked to C-terminus of the peptide.

9. A peptide consisting of the amino acid sequence of SEQ ID NO: 2, wherein a protective group selected from the group consisting of an acetyl group, a fluorenyl methoxy carbonyl group, a formyl group, a palmitoyl group, a myristyl group, a stearyl group, and polyethylene glycol (PEG), is linked to the N-terminus of the peptide.

10. A pharmaceutical composition comprising the peptide of claim 1.

11. A pharmaceutical composition comprising the peptide of claim 8.

12. A pharmaceutical composition comprising the peptide of claim 9.

* * * * *